United States Patent
Moehring et al.

(10) Patent No.: US 11,445,942 B2
(45) Date of Patent: Sep. 20, 2022

(54) ACOUSTIC OTOSCOPE

(71) Applicant: Otonexus Medical Technologies, Inc., Seattle, WA (US)

(72) Inventors: Mark A Moehring, Seattle, WA (US); Jay A. Chesavage, Palo Alto, CA (US); Weigang Wang, Fremont, CA (US); Dong Ho Choi, Palo Alto, CA (US)

(73) Assignee: OtoNexus Medical Technologies, Inc., Bellevue, WA (US)

( * ) Notice: Subject to any disclaimer, the term of this patent is extended or adjusted under 35 U.S.C. 154(b) by 817 days.

(21) Appl. No.: 15/995,793

(22) Filed: Jun. 1, 2018

(65) Prior Publication Data
US 2019/0365292 A1    Dec. 5, 2019

(51) Int. Cl.
  *A61B 5/12*   (2006.01)
  *A61B 5/00*   (2006.01)
  *A61B 1/227*  (2006.01)

(52) U.S. Cl.
  CPC ............. *A61B 5/12* (2013.01); *A61B 1/2275* (2013.01); *A61B 5/0053* (2013.01); *A61B 5/7246* (2013.01)

(58) Field of Classification Search
  CPC ....... A61B 5/12; A61B 1/2275; A61B 5/0053; A61B 5/7246; A61B 5/126
  See application file for complete search history.

(56) References Cited

U.S. PATENT DOCUMENTS

| | | | | |
|---|---|---|---|---|
| 4,237,905 A | * | 12/1980 | Keller | A61B 5/12 600/559 |
| 5,699,809 A | * | 12/1997 | Combs | A61B 5/121 600/558 |
| 5,919,130 A | | 7/1999 | Monroe et al. | |
| 6,126,614 A | * | 10/2000 | Jenkins | A61B 5/01 600/549 |

(Continued)

FOREIGN PATENT DOCUMENTS

| | | |
|---|---|---|
| EP | 0871850 B1 | 12/2002 |
| WO | WO-2009157825 A1 | 12/2009 |
| WO | WO-2019231485 A1 | 12/2019 |

OTHER PUBLICATIONS

"International Search Report for PCT/US2018/051817 dated Nov. 19, 2018".

*Primary Examiner* — Sean P Dougherty
(74) *Attorney, Agent, or Firm* — Wilson Sonsini Goodrich & Rosati

(57) ABSTRACT

An acoustic otoscope generates volume change excitations of either a trapezoidal or sinusoidal waveforms which are coupled into a sealed ear canal using a speculum tip. The change in volume results in a pressure change, for which a pressure measurement is taken during the volume change excitation interval. In one example, a trapezoidal time-domain volume change is presented, and a pressure measurement waveform is stored, the pressure measurement waveform thereafter examined to find a change of slope point in time, after which the pressure measurement wave- (Continued)

form is scaled to be equal to the volume change waveform at that same point in time, a difference between scaled pressure measurement and volume excitation is formed, and examined for peak value prior to the earlier determined change in slope point in time.

21 Claims, 3 Drawing Sheets

(56) References Cited

U.S. PATENT DOCUMENTS

| | | | | |
|---|---|---|---|---|
| 7,399,275 | B2* | 7/2008 | Goldfain | A61B 1/00188 |
| | | | | 600/112 |
| 9,468,400 | B2* | 10/2016 | Lantz | A61B 5/121 |
| 9,867,528 | B1* | 1/2018 | Boppart | A61B 5/0075 |
| 10,568,515 | B2* | 2/2020 | Moehring | A61B 5/7278 |
| 2003/0171655 | A1* | 9/2003 | Newman | A61B 1/227 |
| | | | | 600/200 |
| 2003/0220585 | A1* | 11/2003 | Hissong | A61F 11/00 |
| | | | | 600/560 |
| 2007/0112279 | A1* | 5/2007 | Iseberg | A61B 5/125 |
| | | | | 600/559 |
| 2007/0129632 | A1* | 6/2007 | Voie | A61B 8/4483 |
| | | | | 600/438 |
| 2010/0094137 | A1* | 4/2010 | Furlong | A61B 1/00009 |
| | | | | 600/477 |
| 2010/0191144 | A1 | 7/2010 | Zoth et al. | |
| 2011/0224493 | A1* | 9/2011 | Oyadiran | A61B 5/0084 |
| | | | | 600/200 |
| 2013/0023818 | A1* | 1/2013 | Rosenblum | A61B 5/4839 |
| | | | | 604/28 |
| 2013/0289353 | A1* | 10/2013 | Seth | A61B 5/0084 |
| | | | | 600/200 |
| 2015/0201869 | A1* | 7/2015 | Nikzad | A61B 5/00 |
| | | | | 600/559 |
| 2015/0216452 | A1* | 8/2015 | Smith | A61B 5/126 |
| | | | | 600/559 |
| 2015/0351606 | A1* | 12/2015 | Ruppersberg | A61B 1/07 |
| | | | | 600/200 |
| 2015/0351607 | A1* | 12/2015 | Ruppersberg | A61B 5/01 |
| | | | | 600/473 |
| 2015/0351616 | A1* | 12/2015 | Ruppersberg | A61B 1/00142 |
| | | | | 600/200 |
| 2015/0351637 | A1* | 12/2015 | Ruppersberg | A61B 1/227 |
| | | | | 600/474 |
| 2015/0374208 | A1* | 12/2015 | Ruppersberg | A61B 1/05 |
| | | | | 600/109 |
| 2016/0128555 | A1* | 5/2016 | McMahon | A61B 1/00195 |
| | | | | 600/200 |
| 2017/0014053 | A1 | 1/2017 | Moehring et al. | |
| 2018/0310917 | A1* | 11/2018 | Moehring | B06B 1/0207 |
| 2019/0046089 | A1* | 2/2019 | Pislak | A61B 5/12 |
| 2019/0200873 | A1* | 7/2019 | Chesavage | A61B 5/6817 |
| 2019/0365292 | A1* | 12/2019 | Moehring | A61B 1/2275 |
| 2021/0186426 | A1* | 6/2021 | Raju | A61B 5/6898 |

* cited by examiner

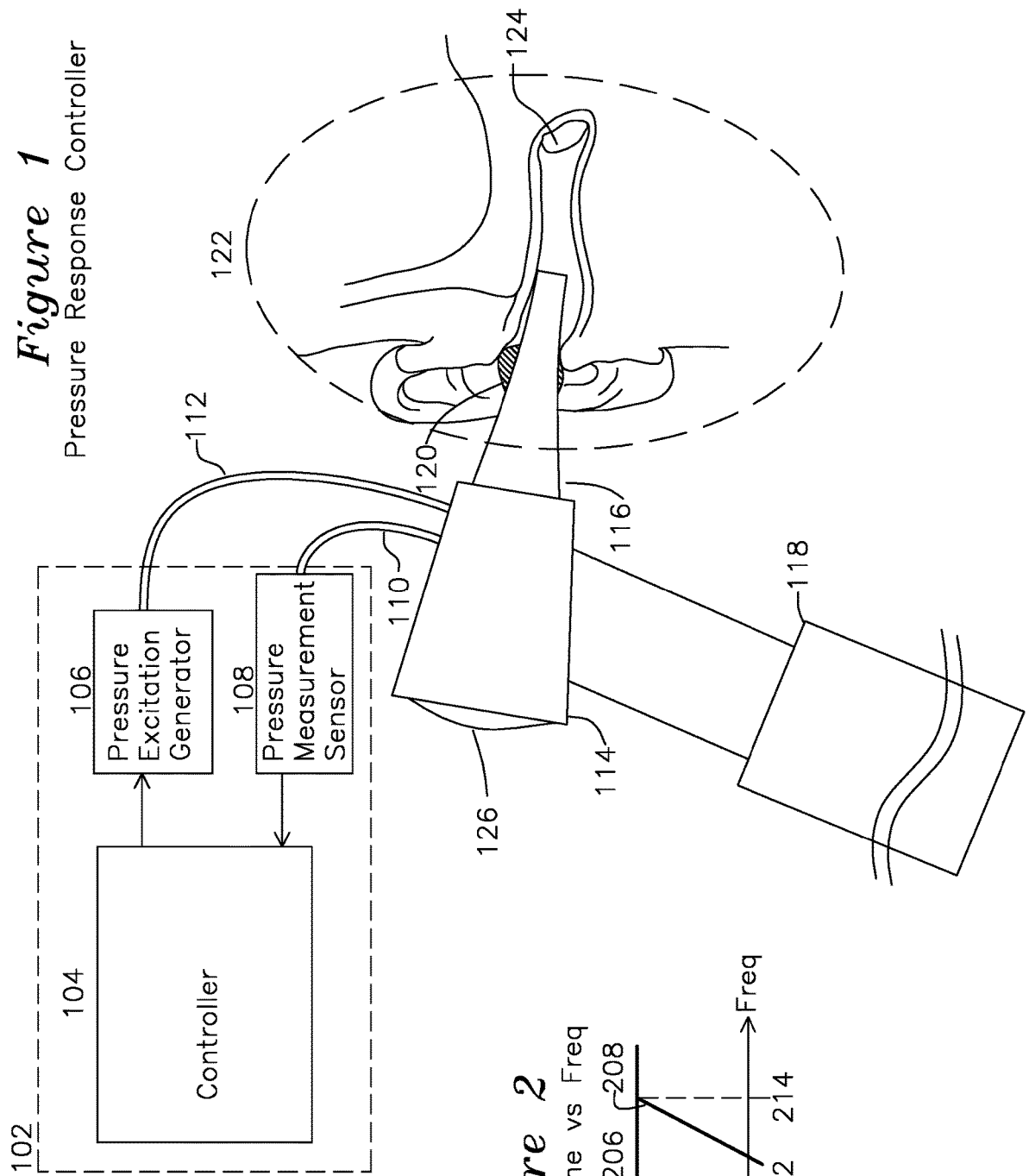

ACOUSTIC OTOSCOPE

FIELD OF THE INVENTION

The present invention relates to an otoscope for characterization of fluid on the proximal surface of a tympanic membrane in a mammalian ear. In particular, the invention relates to making a viscosity measurement of the fluid proximal to the tympanic membrane by measuring the time and frequency related displacement of a tympanic membrane in response to an acoustic volume excitation applied to an ear canal.

BACKGROUND OF THE INVENTION

Acute Otitis Media (AOM) is a common disease of the inner ear, involving tissue inflammation and fluidic pressure which impinges on the tympanic membrane. Acute Otitis Media may be caused by a viral infection, which generally resolves without treatment, or it may be caused by a bacterial infection, which may progress and cause hearing loss or other deleterious and irreversible effects. Unfortunately, it is difficult to distinguish between viral or bacterial infection using currently available diagnostic devices, and the treatment methods for the two underlying infections are quite different. For bacterial infections, antibiotics are the treatment of choice, whereas for viral infections, the infection tends to self-resolve, and antibiotics are not only ineffective, but may result in an antibiotic resistance which would make them less effective in treating a subsequent bacterial infection. It is important to accurately diagnose acute otitis media, as AOM can be a precursor to chronic otitis media with effusion (COME), for which surgical drainage of the effusion and insertion of a tube in the tympanic membrane is indicated.

The definitive diagnostic tool for inner ear infections is myringotomy, an invasive procedure which involves an incision through the tympanic membrane, withdrawal of fluid, and examination of the effusion fluid under a microscope to identify the infectious agent in the effusion. Because of complications from this procedure, it is only used in severe cases. This presents a dilemma for medical practitioners, as the prescription of antibiotics for a viral infection is believed to be responsible for the evolution of antibiotic resistance in bacteria, which may result in more serious consequences later in life, and with no efficacious treatment outcome, as treatment of viral infectious agents with antibiotics is ineffective. An improved diagnostic tool for the diagnosis of acute otitis media is desired.

OBJECTS OF THE INVENTION

A first object of the invention is a device for estimation of tympanic membrane mobility through the introduction of a volume displacement excitation into a sealed ear canal, the measurement of eardrum displacement performed using the proxy of measured pressure in the tympanic membrane.

A second object of the invention is a method for determination viscosity of fluid adjacent to a tympanic membrane by application of a volume displacement excitation and measurement of time and frequency domain characteristics of the pressure developed as a proxy for tympanic membrane displacement.

A third object of the invention is an apparatus for characterization of a fluid adjacent to a tympanic membrane, the apparatus having a speculum tip for sealing an ear canal, a volume displacement source for changing a volume of an ear canal, and a pressure measurement for determining the effect of the displacement change on measured external ear canal ear pressure, thereafter forming an effusion metric based on the amplitude and phase of the pressure response versus time or, equivalently, versus frequency.

SUMMARY OF THE INVENTION

In one example of the invention, a controller is operative to change the air volume of a chamber which is sealed to, and coupled into, an ear canal. The air volume change coupled to the ear canal is referred to as $\Delta V(t)$, a function of time. During the interval of time when the air volume change is occurring, a continuous or discrete series of pressure measurements are made, and the air volume change is compared to the pressure measurements in at least one of a time domain response, or a frequency domain response. In this manner, the extent of displacement of a tympanic membrane in response to the air volume change may be determined, and a viscosity metric may be formed. In alternative embodiments, a pressure modulation may be used which introduces or removes air in a fixed volume to increase or reduce the tympanic membrane pressure.

In another example of the invention, a process for determining the existence or extent of acute otitis media has a cyclic volume displacement step whereby a chamber having a dynamically adjustable internal volume is coupled to a sealed ear canal such as through a speculum tip, the speculum tip including a pressure measurement sensor, the process comparing the change in volume as an excitation source coupled to the ear canal to the change in pressure measured in the ear canal as a response, the time domain static and dynamic response characterized to determine at least one of a frequency response or a time response of the tympanic membrane, the frequency or time response mapped to a mobility metric, from which the presence, absence, or composition of a fluid adjacent to the tympanic membrane may be determined.

BRIEF DESCRIPTION OF THE DRAWINGS

FIG. 1 shows a diagram of a pressure response controller coupled to a human ear canal.

FIG. 2 shows amplitude transfer plots and phase transfer plots for various effusion conditions.

DETAILED DESCRIPTION OF THE INVENTION

Figure 3A:
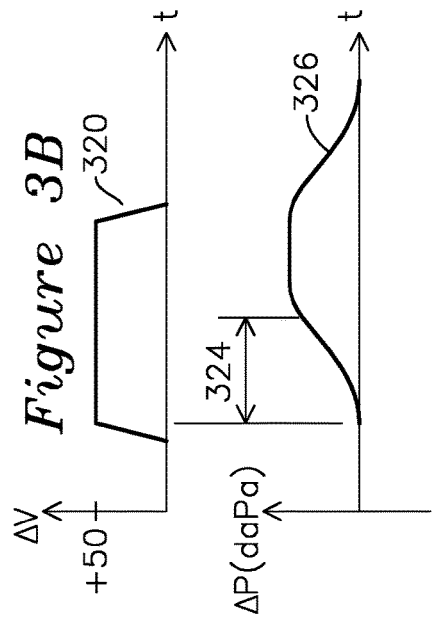
FIGS. 3A, 3B, 4, and 5 show plots for various volume excitation methods and responses.

FIG. 1 shows an otoscope 130 which includes a speculum tip 116 for insertion into an ear canal of a subject to be characterized. A lens 126 is coupled to an optical unit 114 which provides for examination of the outer ear as is provided by a prior art otoscope such as the Welch Allyn 25070-M. A pressure excitation generator 106 couples a volume change from an excitation generator through hose 112 to the speculum tip 116, and a pressure measurement hose to a pressure sensor 108 provides a measurement of pressure change in the speculum tip 116 from the excitation generator change in volume. It may be preferable for the speculum tip 116 to be sealed where it attaches to the optical unit 114 to minimize the volume being excited to include only the ear canal and speculum tip 116 volume, or the speculum tip 116 may be sealed to the ear canal in other locations including the concha and tragus at the entrance to the ear canal or in any location which completes a seal to the ear canal.

When inserted into the ear canal of a subject (detail 122), a conformable seal 120 may be used which comfortably seals the speculum tip 116, thereby providing effective coupling of volume changes generated by volume excitation generator 106 to the inner ear and tympanic membrane 124. Volume (or pressure) excitation generator 106 may be any of: a voice coil integrated with a movable diaphragm, a diaphragm coupled to a piston actuator, or any mechanism modulating a volume or introducing an external pressure source which is coupled to speculum tip 116 to cause a change in pressure (such as by a change in enclosed volume or introduction and removal of a gas such as air from a fixed volume) which couples the change in pressure into the speculum tip 116 and to the tympanic membrane. In the present description, a volume modulating device such as a diaphragm or piston is described, however it is understood that the pressure change generated by the pressure excitation generator 105 may be formed by any volume displacement method. The volume change is intended to result in a very slight change in position of the tympanic membrane 124. If there is no fluid present behind the tympanic membrane 124, the tympanic membrane is able to move freely and accommodate slowly changing (low frequency) changes in volume with negligible changes in pressure. If fluid is present behind the tympanic membrane 124, the tympanic membrane will exhibit reduced displacement for high frequency pressure change. Additionally, for a tympanic membrane which is coupled to watery viral fluid or mucoid infectious fluid, the tympanic membrane may be less able to respond to high frequency changes in volume, which result in greater pressure changes for a given incremental volume change when fluid is present adjacent to the less mobile tympanic membrane, and the greater the mass of the fluid present, the greater the constriction for movement of the tympanic membrane at lower frequencies, resulting in greater induced pressures at greater frequencies.

When fluid is adjacent to the tympanic membrane, the mobility of the tympanic membrane is reduced, which results in greater developed pressure for a given change in volume at high frequencies. This is shown in FIG. 2 frequency response plot showing differential pressure change ($\Delta P$) divided by differential volume change ($\Delta V$) as a function of frequency, scaled to unity for $\Delta P/\Delta V$ of an immobile TM. A pressure change vs volume change response plot for a healthy ear is shown in plot 208, which develops minimal pressure changes for incremental volume change at low frequencies because the mobile tympanic membrane without adjacent fluid coupling tracks displacement changes of the excitation generator, so the volume of the system remains relatively fixed and minimal pressure change results. Fluid adjacent to the TM which adds mass and restricts movement of the TM at higher frequencies results in incremental speculum 116 pressure at lower frequency 212 of plot 206, and "glue ear" where the TM is immobile results in the response plot 204 with associated corner frequency 210, where changes in volume result in greater incremental pressures.

The plots of FIG. 2 show transfer functions of pressure/volume versus frequency such as a sinusoidal volume modulation measured as a transfer function of pressure versus frequency. Each of the plots which has a corner frequency where the transfer function flattens as the frequency is increased. Low frequency volume changes which do not produce a pressure change in the ear indicate the tympanic membrane is moving freely at that frequency, and as the tympanic membrane is unable to move freely because of increased inertia of adjacent fluid coupling, the pressure increases, as shown in the plots of FIG. 2 for various states of the tympanic membrane. For example, a healthy tympanic membrane which is free to move over a wide range of frequencies without resistance is shown as waveform 208 with a corner frequency of 214. Where watery fluid from a viral infection is present behind the tympanic membrane, the mobility of the tympanic membrane 124 is reduced such that it no longer is able to respond to moderate frequencies (212) and develops speculum pressure modulations at these frequencies, as indicated by the pressure/volume response plot 206. The final stage of ear infection, where bacterial matter with greater density than viral watery fluid collects on the tympanic membrane and becomes "glue ear", further reduces the amplitude response and frequency range and is shown with plot 204, indicating that the tympanic membrane does not move in response to volume/pressure excitations except at the lowest pressure excitation frequencies 210. Each corner frequency 210, 212, and 214 is determined by the mass and volume of fluid which restricts the TM movement.

FIG. 3A shows another perspective and method for characterization of the TM using a frequency domain excitation plot 302 (a sinusoidal volume change) with corresponding pressure (used as a proxy for tympanic membrane position) 306. By examination of the amplitude of measured pressure plot 306 and phase delay 310 for a particular period 304, and repeating the measurement at other frequencies, a plot of phase delay 310 and amplitude may be derived from the response waveform 306. In another example embodiment, the phase and amplitude responses may be collected in by using a chirped frequency excitation which varies in period for successive repeated cycles, thereby measuring the tympanic membrane displacement response (via pressure) to a volume excitation (chirped frequency displacement) in a single frequency sweep. The transfer function for the tympanic membrane may be determined as the familiar plot of amplitude of 306 normalized to the amplitude of waveform 302 with phase delay 310 expressed in angle, both measured as a function of frequency. The transfer function amplitude and phase may be used clinically where thresholds are established for frequencies where the amplitude transfer function has dropped 3 dB or 6 dB, or the phase lags by 45 degrees, to establish frequency break points, where the frequency break point may be used as a mobility metric, with a high frequency break point indicating normal ear, a lower frequency break point indicating effusion, and a yet lower frequency break point indicating glue ear.

Figure 3B:
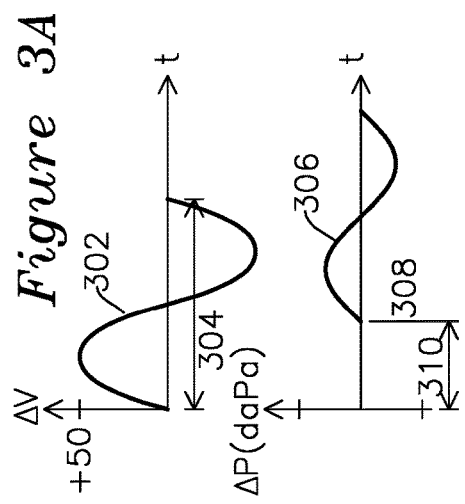
Figure 4:
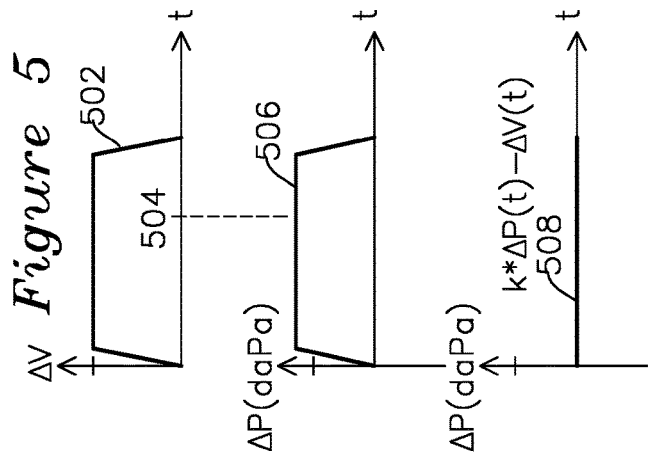
Figure 5:
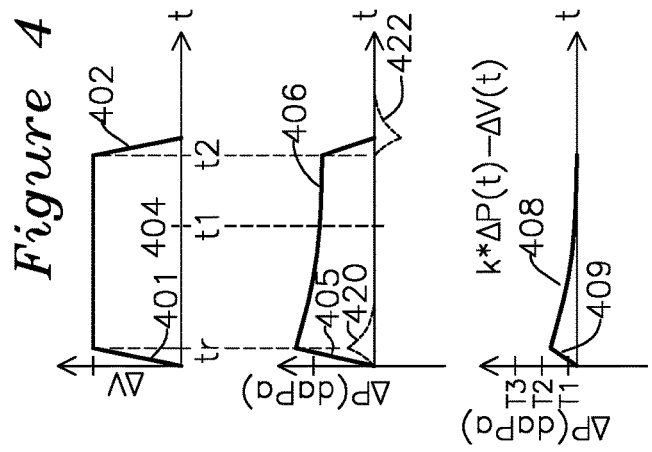

FIG. 3B shows an alternative time domain response, where a step change 320 in volume is momentarily applied, and a pressure response plot 326 is observed, similarly having a time domain delay 324, as well as some rounding of the response associated with loss of high frequency components from the mechanical inertia of the tympanic membrane and adjacent fluid, with the time delay 324 and extent of rounding associated with mobility of the tympanic membrane, which is also a proxy for whether no effusion, watery effusion, or dense bacterial mucoid effusion is present. The measurement metric using the response 326 of FIG. 3B may use time response thresholds to establish health of the tympanic membrane, where a comparatively long time response 324 indicates glue ear, a shorter response indicating effusion, and a yet shorter response indicating a normal ear.

In another measurement method, a trapezoidal pressure excitation 402 is applied by the controller, and the measured pressure 406 in the speculum tip 406 is examined to determine a settling time t1 404 where the temporal rate of change in pressure is reduced to an exemplar ¼ of its initial rate of change value, or is selected to be a particular fixed time 404, whichever occurs first. A scaling factor k is applied to the measured pressure waveform 406 such that the at time t1 404, $k*\Delta P(t1)=\Delta V(t1)$. When k is determined from this measurement, a difference waveform dP(t) 408 is computed, such that $dP(t)=\Delta V(t)-k*\Delta P(t)$. Waveform 408 is examined, and a peak value dP(max) is determined and tested according to the following criteria (where the first threshold, second threshold, and third threshold are established as a monotonically increasing sequence of thresholds):

if dP<T1 (a first threshold), then it is likely no fluid is present;

if T1<=dP<=T2 (a second threshold), it is likely watery fluid is present;

if T2<=dP<=T3 (a third threshold), it is likely mucoid fluid or glue ear is present.

In another example of the invention, the difference dP(t) is formed by averaging several instances of $\Delta V(t)$ and $\Delta P(t)$.

In another example of the invention, the volume excitation $\Delta V(t)$ rise time Tr 401 is varied over several successive cycles in sets, each set of pressure excitations being identical with the pressure response of each cycle averaged to provide a composite $\Delta P(t)$ to provide both a reliable pressure response for each set of cycles, as well as vary the rise time Tr 401 over different sets of measurement cycles to characterize the tympanic membrane for a variety of pressure excitation rise times.

In another example of the invention, delta V rise time 401 is reduced to a minimum and the pressure response rise time 405 from 0 to tr and fall time 406 from tr to t2 are examined and fit to a curve. For example, it may be possible to fit pressure rise time response 405 (or difference rise time 409) to $P_r(t)=k1(1-e^{-t/\tau 1})$ and the fall time 408 to $P_f(t)=k2(e^{-t/\tau 2})$ where:

Pr(t) is rise time of 405 or 409 from 0 to tr;
Pf(t) is the fall time of 406 or 408 offset to 0 at t2;
t is time (x axis of the plots);
k1 is an amplitude scaling constant;
τ1 is the rise time coefficient to be determined by curve fit matching, having units of time;
τ2 is the fall time coefficient to be determined, by curve fit matching, having the units of time.

After determination of k1 and τ1, or k2 and τ2 from at least one of corresponding waveforms 408, 409, 405, or 406, it is then possible to form an effusion metric, where a comparatively longer τ1 or τ2 and a comparatively greater k1 and k2 indicates less likelihood of effusion or glue ear, and a comparatively shorter τ1 or τ2 indicates greater likelihood of effusion, yet shorter τ1 or τ2 indicating glue ear for large values of k1 and k2, and where comparatively smaller values of k1 and k2 may be used to indicate a poor seal (or perforated TM), particularly when accompanied by comparatively short τ1 or τ2.

In another example of the invention, a burst of sinusoidal volume excitation 302 of 5 cycles or more is provided as $\Delta V(t)$, each cycle of the burst being used to average the measured pressure waveform $\Delta P(t)$ for a single cycle at frequency f to provide a pressure response point for a particular frequency f1, thereafter computing the frequency transfer function $$\frac{\Delta P(f1)}{\Delta V(f1)}$$

for each frequency f. The resultant transfer function response corner frequencies 214, 212, 210 of FIG. 2 may thereafter be similarly used as threshold frequencies to determine normal tympanic membrane response, watery fluid behind the tympanic membrane, and mucoid or glue ear tympanic membrane response, respectively.

Each of the above methods as described for FIGS. 2, 3A, 3B, 4, and 5 may be used in a differential method, by comparing results from a left and right ear, in the case where ear infection of only one ear is clinically suspected. The differential comparison method of a healthy appearing ear and an ear suspected of infection may provide normalization of diagnostic thresholds compared to models developed from the general population. For example, a factor of 2 difference in a frequency break point of FIG. 2 or 3A, or a factor of 2 difference in time response of FIG. 3B or 4 between a presumed healthy and suspected infected ear may be used to establish effusion, and a factor of 4 or greater may be used to establish glue ear.

In another embodiment of the invention, the signatures of the pressure responses are examined for evidence of a seal 120 leak. Where a pressure leak to the ear canal is present, the high frequency transfer is adversely affected, if the seal leak is large enough, no pressure will be measured in response to a pressure excitation. An example of a speculum tip leak is shown in the pressure plots 420 and 422 of FIG. 4, where the change in piston/diaphragm volume 402 causes a transient positive pressure 420 followed by a transient negative pressure 422 when the piston/diaphragm moves in the opposite direction. The duration of the measured pressure waveform 420 and 422 may be examined to determine any of several conditions which may identify a poor speculum tip seal 120, not limited to:

1) a shortened pressure time response which is less than a duration of the volume change excitation;

2) the absence of a pressure response during a volume change excitation;

3) A negative pressure response 422 in response to the volume modulating piston/diaphragm being returned to its original position.

Figure 6:
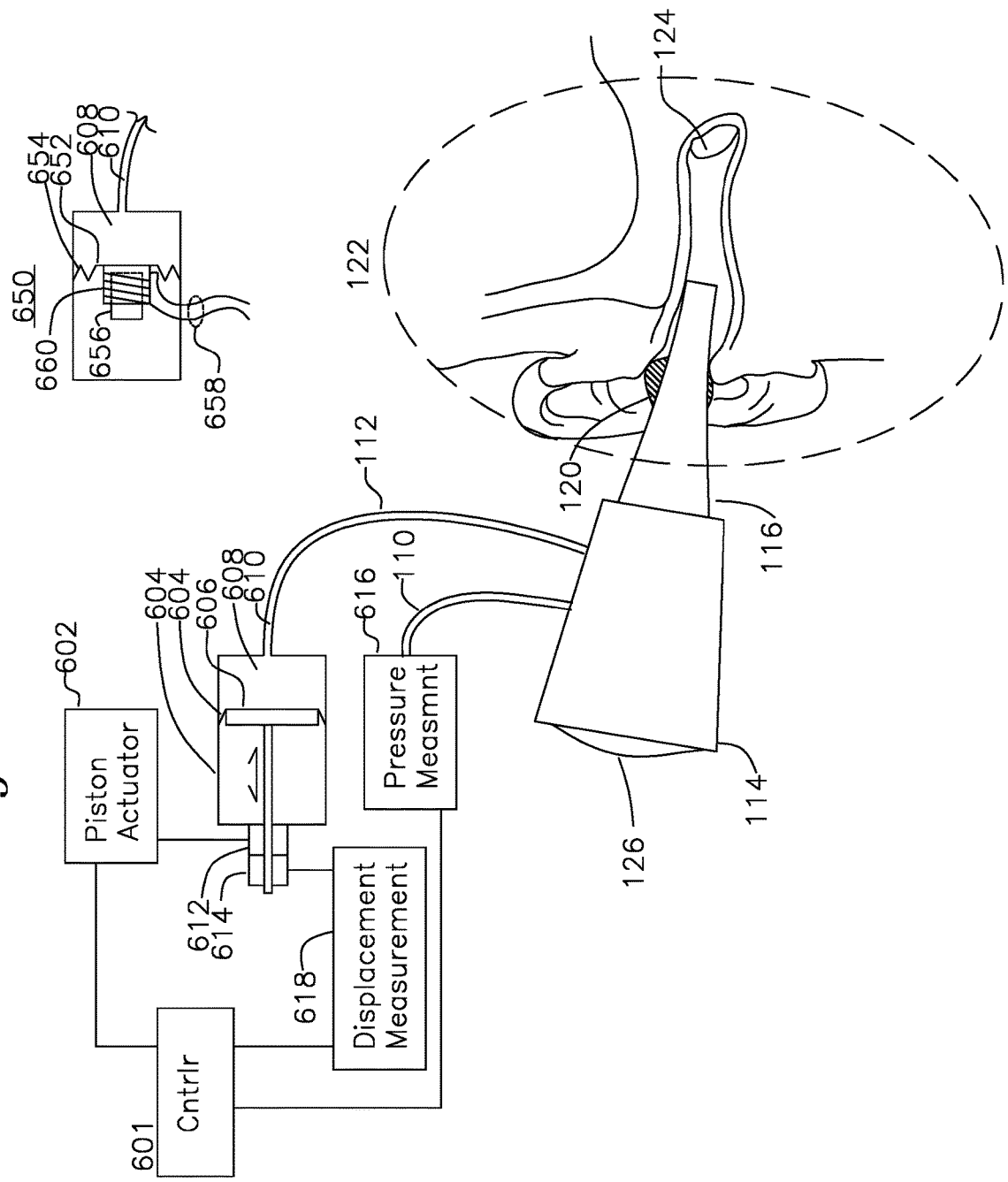
FIG. 6 shows a block diagram of an otoscope measuring a tympanic membrane displacement in response to a displacement source.

FIG. 6 shows an alternative tympanic membrane displacement measurement system comprising piston (or diaphragm) 606 which is sealed 604 to create a closed chamber 608 with the displacement volume coupled via hose 112 to speculum tip 116 with optical viewer 126. Piston actuator 602 (which may be a voice coil actuator or other electromagnetic actuator) causes piston 606 to move along the axis of chamber 608, with the displacement measured by sensor 614 coupled to displacement measurement 618. A central controller 601 issues commands for the piston actuator 602 to cause the piston 606 to modulate position, with the displacement measured 618 and reported to controller 601. The controller 601 also reads a pressure measurement 616 of the pressure developed in the speculum tip 116 delivered from chamber 608 to the speculum tip 116 via hose 112.

In an example embodiment of the invention, the piston diameter 606 is selected to have the same approximate diameter of a pediatric (or adult) tympanic membrane. The piston 606 displacement is modulated and pressure 110 measured. For minimal pressure change and with a sealed system, the output value of displacement measurement 618 may be regarded as a proxy for the tympanic membrane movement. Accordingly, for movement of the piston 608 which generates a minimal change in measured pressure 616, the piston 606 displacement may be regarded as a proxy for the movement of the tympanic membrane. In one example of the invention, the piston 606 displacement is a swept frequency and a break point in the measured pressure measurement 616 frequency response is noted, this frequency break point represents the excitation frequency where the mobility of the tympanic membrane 124 is adversely affected by the mass of adjacent fluid which is preventing the high frequency modulation of the tympanic membrane 124. Alternative diaphragm pressure actuator 603 is shown in view 650, where a voice coil 660 with leads 658 is actuated when a current is developed which causes attraction or repulsion with permanent magnet 656, thereby displacing diaphragm 652 with respect to flexible support 654 which provides high frequency response for diaphragm 652 in enclosed volume 608, with coupling to speculum tip 610 as before, or the excitation generator may be enclosed in speculum tip 116 of FIG. 1, or adjacent enclosure 114.

The illustrative examples are for understanding the invention, the scope of which is set forth in the claims which follow.

We claim:

1. An acoustic otoscope comprising:
   (i) a speculum tip for coupling to an ear canal;
   (ii) a pressure sensor coupled to the speculum tip for estimation of pressure in the speculum tip and providing one or more pressure sensor measurements;
   (iii) an excitation source for generation of dynamic volume or pressure, wherein the excitation source is coupled to the speculum tip for generation of the dynamic volume or pressure in the ear canal; and
   (iv) a controller coupled to the excitation source, wherein the controller is configured to receive the one or more pressure sensor measurements, to compare an excitation source input waveform with a pressure measurement output waveform, and to output an effusion metric based at least in part a comparison of the excitation source input waveform with the pressure measurement output waveform.

2. The acoustic otoscope of claim 1, wherein the controller is configured to output the effusion metric based on one or more difference values generated from subtracting a scaled pressure measurement output waveform from the excitation source input waveform.

3. The acoustic otoscope of claim 2, wherein the effusion metric is derived from the one or more difference values, and wherein the one or more difference values has an elevated amplitude following a step change in pressure or volume compared to a subsequent difference value.

4. The acoustic otoscope of claim 2, wherein the effusion metric is derived from the one or more difference values, and wherein the one or more difference values has an elevated amplitude for a low frequency pressure or volume excitation compared to an amplitude for a high frequency pressure or volume excitation.

5. The acoustic otoscope of claim 2, wherein the one or more difference values is averaged over at least 4 acquisition cycles.

6. The acoustic otoscope of claim 2, wherein the scaled pressure measurement output waveform comprises a scaling factor, and wherein the one or more pressure measurements has a mid-point value substantially equal to a mid-point input value of the excitation source input waveform.

7. The acoustic otoscope of claim 1, wherein the excitation source input waveform is sinusoidal.

8. The acoustic otoscope of claim 1, wherein the excitation source input waveform is trapezoidal.

9. The acoustic otoscope of claim 7, wherein the sinusoidal excitation source input waveform and the pressure measurement output waveform are acquired over several frequencies to determine a corner frequency.

10. The acoustic otoscope of claim 9, wherein the effusion metric comprises a comparison of the corner frequency to a threshold frequency corresponding to one or more of a normal tympanic membrane, a viral fluid adjacent to a tympanic membrane, or a mucoid fluid adjacent to a tympanic membrane.

11. The acoustic otoscope of claim 1, wherein the excitation source comprises:
   a moveable diaphragm,
   a moveable piston, or
   a source of differential pressure coupled to the speculum tip with a hose.

12. The acoustic otoscope of claim 1, wherein the excitation source comprises a diaphragm or piston enclosed in the speculum tip or a mount for the speculum tip.

13. The acoustic otoscope of claim 1, wherein the excitation source is coupled to a source of greater or lower air pressure through one or more valves.

14. An acoustic otoscope having:
   a speculum tip configured to form a seal when inserted into an ear canal;
   an excitation source coupled to the speculum tip and configured to modulate a pressure within the ear canal,
   a pressure sensor coupled to the speculum tip and configured to measure the pressure within the ear canal; and
   a controller coupled to the pressure sensor and configured to (i) generate an excitation source input waveform and (ii) receive a pressure measurement output waveform;
   wherein the controller is configured to: determine an effect of the excitation source input waveform on the pressure measurement output waveform, compare the pressure measurement output waveform with the excitation source input waveform, and generate an effusion metric based at least in part on a comparison of the excitation source input waveform with the pressure measurement output waveform.

15. The acoustic otoscope of claim 14, wherein the excitation source is configured to cause a volume change or a pressure change within the ear canal.

16. The acoustic otoscope of claim 14, wherein the excitation source is a moving diaphragm.

17. The acoustic otoscope of claim 14, wherein, after a monotonic pressure sequence of a first threshold, a second threshold, and a third threshold are established, the effusion metric is used to identify a non-diagnostic speculum top leak when:
   (i) a transfer function for the pressure measurement output waveform to the excitation source input waveform is below the first threshold;
   (ii) a high frequency transfer function for the pressure measurement output waveform to the excitation source input waveform is below the third threshold;
   (iii) a negative pressure response is detected when the excitation source is a volume modulating piston or diaphragm which is returned to an original position; or (iv) a pressure measurement change is not detected in response to the excitation source waveform.

18. The acoustic otoscope of claim 14, wherein the excitation source input waveform is a sinusoid and the effusion metric is based on a corner frequency in a frequency response function $$\frac{\Delta P(f)}{\Delta V(f)}$$

where:
- $\Delta P(f)$ is a pressure amplitude for a plurality of discrete frequencies;
- $\Delta V(f)$ is a volume excitation amplitude for a plurality of discrete frequencies; and
- the corner frequency is a frequency f for which the frequency response function is less than $1/\sqrt{2}$ of a value at a higher frequency.

19. The acoustic otoscope of claim 14, wherein the excitation source input waveform is a trapezoidal waveform, wherein the effusion metric is based on a difference waveform, wherein the difference waveform is a difference between the excitation source input waveform and the pressure measurement output waveform, and wherein the pressure output measurement waveform is scaled to a midpoint of the excitation source input waveform.

20. The acoustic otoscope of claim 19, wherein the midpoint is an earliest of a point in time where a slope of the pressure measurement output waveform changes to ¼ or less of its initial value or a half interval point, whichever occurs sooner.

21. The acoustic otoscope of claim 19, wherein the effusion metric is based on a maximum amplitude of the difference waveform before the midpoint.

* * * * *